US006084117A

United States Patent [19]
Berris et al.

[11] Patent Number: 6,084,117
[45] Date of Patent: Jul. 4, 2000

[54] PRODUCTION OF SILATED HALOARENES BY SELECTIVE SILYLATION OF POLYHALOARENES

[75] Inventors: Bruce C. Berris; David W. Owens; Rajeev S. Mathur, all of Baton Rouge, La.

[73] Assignee: Albemarle Corporation, Richmond, Va.

[21] Appl. No.: 09/444,765

[22] Filed: Nov. 22, 1999

[51] Int. Cl.⁷ ..................................................... C07F 7/08
[52] U.S. Cl. .............................................................. 556/478
[58] Field of Search .............................................. 556/478

[56] References Cited

U.S. PATENT DOCUMENTS

| | | | |
|---|---|---|---|
| 3,485,863 | 12/1969 | Nutzel et al. ............................ | 556/478 |
| 4,171,360 | 10/1979 | Hill ......................................... | 424/245 |
| 5,359,065 | 10/1994 | Krishnamurthy ..................... | 556/478 X |
| 5,498,739 | 3/1996 | Takeuchi et al. ....................... | 556/478 |
| 5,589,500 | 12/1996 | Edwards et al. ........................ | 514/428 |
| 5,780,473 | 7/1998 | Murugesan et al. .................... | 514/252 |

OTHER PUBLICATIONS

Kurata et al., "Tandem Reactions of N,N–Dialkylamides With Organolithium Compounds and Cyclopentadiene. A New Efficient Synthesis of Pentafulvenes", Tetrahedron Letters, Jun. 1993, vol. 34, No. 21, pp. 3445–3448.

*Primary Examiner*—Paul F. Shaver
*Attorney, Agent, or Firm*—Philip M. Pippenger

[57] ABSTRACT

Lithiated haloarenes, although useful as intermediates in the synthesis of various end products, can be hazardous to prepare since unstable, shock sensitive compounds can be formed during lithiation of haloarenes. To avoid this problem, a reaction of a polyhaloarene with a hydrocarbyl lithium compound is conducted in the presence of another reactant so that the lithiated haloarene, if formed at all, exists as a transitory intermediate in low concentration. In this way, transitory lithiated haloarene which may be, and presumably is, formed in the reaction is converted into a non-hazardous functionally-substituted haloarene essentially as soon as such lithiated haloarene is formed. Thus, an arene having a halogen atom of atomic number greater than 9 substituted on at least two non-adjacent carbon atoms is concurrently reacted with a non-fluoro halotrihydrocarbylsilane and a hydrocarbyl lithium compound, in proportions such that a haloarene having at least one trihydrocarbylsilyl ring substituent is formed.

41 Claims, No Drawings

PRODUCTION OF SILATED HALOARENES BY SELECTIVE SILYLATION OF POLYHALOARENES

BACKGROUND

Lithiated haloarenes are useful as intermediates in the synthesis of various end products, such as ligands for metallocene polymerization catalysts, and starting materials for the synthesis of agricultural chemicals and pharmaceuticals. Unfortunately, however, lithiation of polyhaloarenes, can be hazardous since unstable, shock sensitive compounds can be formed in this manner.

SUMMARY OF THE INVENTION

This invention involves the discovery that it is possible to avoid such hazards by conducting the reaction of a polyhaloarene with a hydrocarbyl lithium compound in the presence of another reactant so that the lithiated haloarene, if formed at all, exists as a transitory intermediate in low concentration. In this way, transitory lithiated haloarene which may be, and presumably is, formed in the reaction is converted into a non-hazardous functionally-substituted haloarene essentially as soon as such lithiated haloarene is formed.

More particularly, this invention provides in one of its embodiments a process which comprises concurrently reacting (i) an arene having a halogen atom of atomic number greater than 9 substituted on at least two non-adjacent carbon atoms with (ii) a halotrihydrocarbylsilane in which the halogen atom has an atomic number greater than 9, and (iii) a hydrocarbyl lithium compound, in proportions such that a haloarene having at least one trihydrocarbylsilyl ring substituent is formed. To minimize interaction between (ii) and (iii), it is preferable to perform the reaction by adding (iii) to a mixture of (i) and (ii). However it is also possible to perform the reaction by concurrently but separately adding (ii) and (iii) to (i).

Another embodiment of this invention is a process which comprises forming a mixture from components comprising (i) an arene having a halogen atom of atomic number greater than 9 substituted on at least two non-adjacent carbon atoms with (ii) a halotrihydrocarbylsilane in which the halogen atom has an atomic number greater than 9, and (iii) a hydrocarbyl lithium compound, with the proviso that (ii) and (iii) are not mixed together in the absence of (i), and wherein these components are proportioned such that reaction takes place and a haloarene having at least one trihydrocarbylsilyl ring substituent is formed. Typically the reaction engendered in this manner requires no application of heat energy to the reaction mixture. In fact, it is preferred to initiate the reaction at temperatures below room temperature to ensure that the reaction does not proceed at an overly-rapid rate.

Still another embodiment is to react a hydrocarbyl lithium compound with a haloarene having at least one trihydrocarbylsilyl ring substituent formed pursuant to this invention, to form a lithiated haloarene having at least one trihydrocarbylsilyl ring substituent. This in turn enables the product ion of still other desirable compounds. For example, in a preferred embodiment of this invention the following sequence of reactions is performed:

A) forming a mixture from components comprising (i) 1,4-dihalobenzene such as 1,4-dibromobenzene, (ii) a chlorotrialkylsilane or a bromotrialkylsilane in which the alkyl groups each contain in the range of 1 to about 4 carbon atoms, and (iii) a hydrocarbyl lithium compound, with the proviso that (ii) and (iii) are not mixed together in the absence of (i), and wherein these components are proportioned such that reaction takes place and a 4-halo-1-(trialkylsilyl)benzene is formed;

B) forming a mixture of 4-halo-1-(trialkylsilyl)benzene from A) and a hydrocarbyl lithium compound such that the halogen atom of the 4-halo-1-(trialkylsilyl)benzene is replaced by a lithium atom thereby forming a 4-lithio-1-(trialkylsilyl)benzene;

C) forming a mixture of 4-lithio-1-(trialkylsilyl)benzene from B) and a dihydrocarbylcarbamyl halide such that bis(4-trialkylsilylphenyl)dihydrocarbylamidomethoxy lithium, a tertiary alkoxide intermediate is formed; and D) forming a mixture of bis(4-trialkylsilylphenyl) dihydrocarbylamidomethoxy lithium from C) and monomeric substituted or unsubstituted cyclopentadiene or indene hydrocarbon such that a 6,6-di(4-(trialkylsilylphenyl)pentafulvenoid compound is formed.

Most preferably steps A) through D) are conducted in the same reactor without isolation of the reaction products from A), B) or C). In addition, it is particularly preferred to conduct steps A) through C) in an ether solvent other than tetrahydrofuran so that the reactions can be initiated and performed at temperatures near 0° C. without by-product bromohydrocarbon reacting with haloaryllithium or hydrocarbyllithium. Suppression of such adverse side reactions in the presence of tetrahydrofuran requires temperatures below about −50° C. Tetrahydrofuran can, however, be utilized to advantage in the conduct of step D).

The above and other embodiments and features of this invention will be still further apparent from the ensuing description and appended claims.

FURTHER DETAILED DESCRIPTION

Concurrent Lithiation and Silvlation Processes

One or a mixture of arenes having a halogen atom of atomic number greater than 9 substituted on at least two non-adjacent carbon atoms are used as one of the reactants in the processes of this invention. While such haloarene can contain inert ring substitution as well as the two or more halogen atoms individually substituted on non-adjacent carbon atoms, preferably the haloarene reactant is free of substitution by functional groups other than the halogen atom of atomic number greater than 9 substituted on at least two non-adjacent carbon atoms.

Illustrative examples of such haloarenes include 1,3-dihalobenzenes, 1,4-dihalobenzenes, 1-hydrocarbyl-3,5-dihalobenzenes (e.g., where the hydrocarbyl group in the 1-position is an alkyl, cycloalkyl, aryl, aralkyl, or other univalent group consisting of carbon and hydrogen atoms and that is either saturated or that contains only aromatic unsaturation), 1,3,5-trihalobenzenes, dihalobiphenyls in which one halogen atom is on each ring, trihalobiphenyls in which two halogen atoms are on one ring and one halogen atom is on the other ring, tetrahalobiphenyls in which three halogen atoms are on one ring and one halogen atom is on the other ring, tetrahalobiphenyls in which two halogen atoms are on one ring and two halogen atoms are on the other ring, pentahalobiphenyls in which three halogen atoms are on one ring and two halogen atoms are on the other ring, hexahalobiphenyls in which three halogen atoms are on one ring and three halogen atoms are on the other ring, dihalonaphthalenes in which one halogen atom is on each ring, dihalonaphthalenes in which both halogen atoms are on the same ring, trihalonaphthalenes in which two halogen atoms are on one ring and one halogen atom is on the other ring, tetrahalonaphthalenes in which two halogen atoms are on one ring and two halogen atoms are on the other ring, or a mixture of any two or more of the foregoing. Typically the haloarene reactant will contain at least two ring halogen atoms and in the range of 6 to about 24 carbon atoms in the molecule. While the halogen atoms can be iodine atoms or mixtures of two or all three of the halogens, chlorine, bromine and iodine atoms, the preferred reactants are those in which all ring halogen atoms thereof are chlorine atoms or bromine atoms. One particularly preferred reactant is 1,4-dibromobenzene.

A second reactant in the processes of this invention is a halotrihydrocarbylsilane in which the halogen atom has an atomic number greater than 9. The halogen atom can be an iodine atom, but preferably is a bromine or especially, a chlorine atom. Each hydrocarbyl group is typically an alkyl, cycloalkyl, aryl, aralkyl, or other univalent group consisting of carbon and hydrogen atoms, and preferably is one that is either saturated or that contains only aromatic unsaturation and contains no more than about 36 carbon atoms. Bromotrialkylsilanes and chlorotrialkylsilanes in which each alkyl group contains up to about 12 carbon atoms are particularly preferred.

The third reaction component used in the process is a hydrocarbyl lithium compound such a a lithium alkyl. Lithium alkyls in which the alkyl group has up to about 10 carbon atoms are preferred. Most preferred are lithium alkyls having in the range of 1 to 4 carbon atoms in the alkyl group. The hydrocarbyl lithium reactant can be, and typically is, used in the form of a solution in an inert solvent such as a paraffinic hydrocarbon.

The reaction is performed in the liquid phase and thus an inert solvent is typically used as a liquid reaction medium. Preferred solvents are one or more liquid aliphatic monoethers or polyethers, or one or more liquid paraffinic, cycloparaffinic or aromatic hydrocarbons, or mixtures of such ethers and/or such hydrocarbons. However other inert solvents can be used if desired.

As noted above, the reaction is preferably initiated at a temperature below room temperature—i.e., preferably the reaction is initiated at a temperature below about 20° C., and preferably is initiated at a temperature in the range about 10 to about 15° C. However, it is possible to initiate the reaction at higher temperatures than these, provided that care is taken to ensure that the reaction does not become uncontrollable. Pressure is not an important factor in the conduct of the process.

The process produces a haloarene in which at least one ring halogen atom of the initial haloarene reactant has been replaced by a trihydrocarbylsilyl ($R_3Si$—) group. Depending on the proportions used, more than one such halogen atom can be so-replaced. However the reaction can be conducted such that at least one ring halogen atom of the haloarene reactant remains on the ring. Accordingly, the reactants are proportioned such that the desired number of ring halogen atoms are replaced by trihydrocarbylsilyl groups. The halotrihydrocarbylsilane and the hydrocarbyl lithium compound are usually employed in approximately equimolar amounts relative to each other, e.g., in a mole ratio of about 0.8–1.2:1, and most preferably about 1:1. Likewise the molar amount of the halotrihydrocarbylsilane relative to the haloarene reactant used is typically approximately equivalent to the number of moles of ring halogen atoms to be replaced by trihydrocarbylsilyl groups. For example if the haloarene is a dihaloarene, one halogen atom is to be replaced by a trihydrocarbylsilyl group, and thus the molar ratio of the dihaloarene to the halotrihydrocarbylsilane should be about 1:1. In such case the preferred molar ratio of the dihaloarene:halotrihydrocarbylsilane:hydrocarbyl lithium compound (RLi) is about 1:1:1. In the case where the haloarene contains, say, three ring halogen atoms, the molar ratio will depend upon the product desired. If only one ring halogen atom is to be replaced, the preferred molar ratio of the dihaloarene:halotrihydrocarbylsilane:hydrocarbyl lithium compound (RLi) is about 1:1:1. But if two of the ring halogen atoms are to be replaced, then the preferred dihaloarene:halotrihydrocarbylsilane:hydrocarbyl lithium compound (RLi) mole ratio is about 1:2:2 (or 0.5:1:1), respectively. Small variations in proportions are acceptable but in general should be kept to a minimum if product of highest purity is desired.

Reaction time depends somewhat on temperature of the reaction mass. However, with reactions performed at about 10 to about 15° C. times in the range of about 0.5 to about 2 hours are usually suitable to achieve good yields. The process can be monitored by GC analysis of samples taken during the reaction.

Subsequent Lithiation Process

Any of the above hydrocarbyl lithium compounds can be employed in the embodiment of this invention wherein a hydrocarbyl lithium compound is reacted with a haloarene having at least one trihydrocarbylsilyl ring substituent formed pursuant to this invention to form a lithiated haloarene having at least one trihydrocarbylsilyl ring substituent. Preferably this reaction is conducted in the same reaction vessel as the reaction in which the haloarene having at least one trihydrocarbylsilyl ring substituent was formed. It is unnecessary to isolate the halo(trihydrocarbylsilyl)arene formed by use of the above concurrent lithiation and silylation process of this invention.

This lithiation process provides a lithiated product which is amenable to a wide variety of reactions to produce useful end products in which the trihydrocarbylsilyl ring substituent(s) remain(s) in the product or in which such substituent(s) no longer remain(s) in the product. One especially desirable use of the subsequent lithiation process of this invention is in a sequence of reactions for the production of 6,6-di(4-(trialkylsilylphenyl)pentafulvenoids. Such pentafulvenoids can in turn be converted by reaction with lithiated fluorenides directly into cyclopentadienyl-fluorenyl ligands useful in the production of bridged metallocene olefin polymerization catalysts.

Production of 6,6-Di(4-(trialkylsilylphenyl)pentafulvenoids

It will be recalled that these pentafulvenoids are produced pursuant to this invention by a process which comprises:

A) forming a mixture from components comprising (i) 1,4-dihalobenzene such as 1,4-dibromobenzene, (ii) a chlorotrialkylsilane or a bromotrialkylsilane in which the alkyl groups each contain in the range of 1 to about 12 carbon atoms, and (iii) a hydrocarbyl lithium compound, with the proviso that (ii) and (iii) are not mixed together in the absence of (i) (preferably by adding (iii) to a mixture of (i) and (ii)), and wherein these components are proportioned such that reaction takes place and a 4-halo-1-(trialkylsilyl)benzene is formed;

B) forming a mixture of 4-halo-1-(trialkylsilyl)benzene from A) and a hydrocarbyl lithium compound (preferably by adding the hydrocarbyl lithium compound to the 4-halo-1-(trialkylsilyl)benzene without isolating the latter), such that the halogen atom of the 4-halo-1-(trialkylsilyl)benzene is replaced by a lithium atom thereby forming a 4-lithio-1-(trialkylsilyl)benzene;

C) forming a mixture of 4-lithio-1-(trialkylsilyl)benzene from B) and a dihydrocarbylcarbamyl halide (preferably by adding the dihydrocarbylcarbamyl halide to the 4-lithio-1-(trialkylsilyl)benzene without isolating the latter), such that bis(4-trialkylsilylphenyl) dihydrocarbylamidomethoxy lithium is formed; and D) forming a mixture of bis(4-trialkylsilylphenyl) dihydrocarbylamidomethoxy lithium from C) and monomeric substituted or unsubstituted cyclopentadiene or indene hydrocarbon (preferably by adding the cyclopentadiene or indene hydrocarbon to the 4,4'-(trialkylsilyl) diphenylketone without isolating the latter) such that a 6,6-di(4-(trialkylsilylphenyl)pentafulvenoid compound is formed.

Each of the reactions of A), B), C), and D) is preferably initiated at a temperature below about 25° C., but can be performed, respectively, at temperatures in ranges of about 0 to about 20° C., about 0 to about 40° C., about 0 to about 40° C., and about 10 to about 40° C. It is particularly preferred to conduct steps A) through C) in an ether solvent other than tetrahydrofuran so that the reactions can be initiated and performed at temperatures near 0° C. without by-product bromohydrocarbon reacting with haloaryllithium or hydrocarbyllithium. Suppression of such adverse side reactions in the presence of tetrahydrofuran requires temperatures below −50° C. Tetrahydrofuran can, however, be utilized to advantage in the conduct of step D).

The dihydrocarbylcarbamyl halide reactant used in step C) has a halogen atom of atomic number above 9, preferably a bromine atom, and most preferably a chlorine atom. The hydrocarbyl groups can be alkyl, cycloalkyl, aryl, aralkyl, or other univalent group consisting of carbon and hydrogen atoms, and preferably is one that is either saturated or that contains only aromatic unsaturation and contains no more than about 18 carbon atoms. Preferred are dialkylcarbamyl bromides, and especially dialkylcarbamyl chlorides. The most preferred reactants for the reaction of step C) are dimethylcarbamyl chloride, and diethylcarbamyl chloride.

Of the monomeric substituted or unsubstituted cyclopentadiene hydrocarbons used as the reactant in step D), freshly prepared monomeric cyclopentadienyl hydrocarbons are preferred. Such compounds are typically prepared by thermal treatment of a dimeric cyclopentadiene hydrocarbon to "crack" the dimer and thereby produce the monomeric form. Examples of suitable monomeric cyclopentadiene hydrocarbons include cyclopentadiene, methylcyclopentadiene, dimethylcyclopentadiene, trimethylcyclopentadiene, tetramethylcyclopentadiene, and corresponding higher alkyl-substituted cyclopentadienes, as well as cycloalkyl-substituted cyclopentadienes, aryl-substituted cyclopentadienes, and cyclopentadiene substituted by one or more other hydrocarbyl groups such as benzyl, vinyl, allyl, or cyclopropylcarbinyl. Cyclopentadiene hydrocarbons having at least two different hydrocarbyl substituents on the ring can also be used. Typically the monomeric cyclopentadiene hydrocarbon will contain in the range of 5 to about 18 carbon atoms in the molecule, and of these cyclopentadiene and the methyl-substituted cyclopentadienes are preferred.

It is also possible pursuant to this invention to use in step D) monomeric cyclopentadiene substituted by one or more functional groups which do not interfere with the reaction of step D). In such cases the functional substituent(s) on the cyclopentadiene reactant will remain in the resultant 6,6-di (4-(trialkylsilylphenyl)pentafulvenoid compound. Examples of such substituents include, for example, alkoxy (methoxy, ethoxy) and aryloxy (phenoxy), dialkylamino (dimethylamino, diethylamino) and diarylamino (diphenylamino).

The following Example is illustrates the practice and advantages of various embodiments of this invention. This Example is presented for the purposes of illustration, and is not intended to limit, and should not be construed as limiting, the scope of this invention.

EXAMPLE

A flask was charged with a solution of 2.59 g of 1,4-dibromobenzene (11.0 mmol) and 1.69 g of chlorotriethylsilane (11.0 mmol) in 25 g of ether. The mixture was cooled to 15° C. and 4.4 mL of 2.5 M n-BuLi in hexanes (11.0 mmol) were added. A sample analyzed by GC showed 91% 4-bromotriethylsilylbenzene, 4% dibromobenzene, and 5% 4-bis(triethylsilyl)benzene. Another 4.4 mL of BuLi solution at 15° C. was added and the mixture stirred at room temperature for one hour. (A sample was removed to check for completeness of the lithiation by GC, after quenching the sample with water. Upon completion, the quenched reaction mixture showed only a trace of 4-bromotriethylsilylbenzene and mainly triethylsilylbenzene). Dimethylcarbamyl chloride (0.57 g 5.3 mmol) was added while cooling the reaction mixture in ice, and the mixture stirred for one hour at room temperature. With stirring, 0.93 g (14.1 mmol) of freshly cracked cyclopentadiene and 11 g of THF were added. The reaction mixture turned yellow-orange in a few minutes. After 5 h, the reaction mixture was treated with 19 g of water, the organic phase isolated and washed with 14 g of water. Toluene (26 g) was added and the reaction mixture was concentrated in a vacuum leaving 4.3 g of red liquid, 84 wt % of the 6,6-di(4-(triethylsilylphenyl)pentafulvenoid product having the formula:

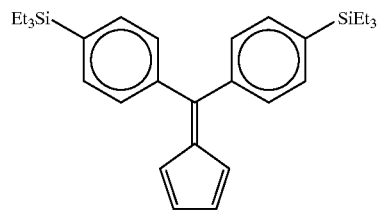

It is not necessary to carry out the aqueous workup procedure described in the above example. The reaction mass produced from the reaction with cyclopentadiene, preferably after filtration, can be subjected to further reactions to produce the desired end product. For example, the reaction mass can be treated with lithium fluorenides to make cyclopentadienyl-fluorenyl ligands directly.

It will be seen from the above Example that the concurrent lithiation and silylation reactions are made possible by the facts that:

1) lithiation of the 1,4-dibromobenzene is faster than lithiation of 4-bromotriethylsilylbenzene. Otherwise, 1,4-bis(triethylsilyl)benzene would form. Only small amounts of this impurity were noted.

2) silylation of 4-bromophenyllithium is faster than silylation of butyllithium. Otherwise, butyltriethylsilane would form.

3) lithiation of 4-bromophenyllithium is slower than its silylation. If the lithiation were faster, this would also result in formation of 1,4-bis(triethylsilyl)benzene.

Thus, the reaction rates are such that they work in concert to produce a high yield of the desired halo (trihydrocarbylsilyl)arene.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises concurrently reacting (i) an arene having a halogen atom of atomic number greater than 9 substituted on at least two non-adjacent carbon atoms with (ii) a halotrihydrocarbylsilane in which the halogen atom has an atomic number greater than 9, and (iii) a hydrocarbyl lithium compound, in proportions such that a haloarene having at least one trihydrocarbylsilyl ring substituent is formed.

2. A process according to claim 1 wherein the reaction is performed by adding (iii) to a mixture of (i) and (ii).

3. A process according to claim 1 wherein the reaction is performed by concurrently but separately adding (ii) and (iii) to (i).

4. A process according to claim 1 wherein (i) is free of substitution by functional groups other than said halogen atom of atomic number greater than 9 substituted on at least two non-adjacent carbon atoms.

5. A process according to claim 1 wherein at least two of said non-adjacent carbon atoms of (i) are each substituted by a chlorine atom or by a bromine atom.

6. A process according to claim 1 wherein (i) is free of substitution by functional groups other than said halogen atom of atomic number greater than 9 substituted on at least two non-adjacent carbon atoms, and wherein each said halogen atom of (i) is either a bromine atom or a iodine atom.

7. A process according to claim 1 wherein the halotrihydrocarbylsilane of (ii) is a chlorotrihydrocarbylsilane in which each hydrocarbyl group has in the range of 1 to about 12 carbon atoms, or a bromotrihydrocarbylsilane in which each hydrocarbyl group has in the range of 1 to about 12 carbon atoms.

8. A process according to claim 1 wherein the hydrocarbyl lithium compound of (iii) is a lithium alkyl having in the range of 1 to about 10 carbon atoms in the molecule.

9. A process according to claim 6 wherein the reaction is performed by adding (iii) to a mixture of (i) and (ii).

10. A process according to claim 7 wherein the reaction is performed by adding (iii) to a mixture of (i) and (ii).

11. A process according to claim 8 wherein the reaction is performed by adding (iii) to a mixture of (i) and (ii).

12. A process according to claim 1 wherein (i) is free of substitution by functional groups other than said halogen atom of atomic number greater than 9 substituted on at least two non-adjacent carbon atoms, wherein each said halogen atom of (i) is either a chlorine atom or a bromine atom, and wherein the halotrihydrocarbylsilane of (ii) is a chlorotrihydrocarbylsilane in which each hydrocarbyl group has in the range of 1 to about 12 carbon atoms, or a bromotrihydrocarbylsilane in which each hydrocarbyl group has in the range of 1 to about 12 carbon atoms.

13. A process according to claim 1 wherein (i) is free of substitution by functional groups other than said halogen atom of atomic number greater than 9 substituted on at least two non-adjacent carbon atoms, wherein each said halogen atom of (i) is either a bromine atom or a iodine atom, and wherein the hydrocarbyl lithium compound of (iii) is a lithium alkyl having in the range of 1 to about 10 carbon atoms in the molecule.

14. A process according to claim 1 wherein the halotrihydrocarbylsilane of (ii) is a chlorotrihydrocarbylsilane in which each hydrocarbyl group has in the range of 1 to about 8 carbon atoms, or a bromotrihydrocarbylsilane in which each hydrocarbyl group has in the range of 1 to about 8 carbon atoms, and wherein the hydrocarbyl lithium compound of (iii) is a lithium alkyl having in the range of 1 to about 6 carbon atoms in the molecule.

15. A process according to claim 12 wherein the reaction is performed by adding (iii) to a mixture of (i) and (ii).

16. A process according to claim 13 wherein the reaction is performed by adding (iii) to a mixture of (i) and (ii).

17. A process according to claim 14 wherein the reaction is performed by adding (iii) to a mixture of (i) and (ii).

18. A process according to claim 1 wherein (i) is free of substitution by functional groups other than said halogen atom of atomic number greater than 9 substituted on at least two non-adjacent carbon atoms, wherein each said halogen atom of (i) is either a chlorine atom or a bromine atom, wherein the halotrihydrocarbylsilane of (ii) is a chlorotrihydrocarbylsilane in which each hydrocarbyl group has in the range of 1 to about 8 carbon atoms, or a bromotrihydrocarbylsilane in which each hydrocarbyl group has in the range of 1 to about 8 carbon atoms, and wherein the hydrocarbyl lithium compound of (iii) is a lithium alkyl having in the range of 1 to about 6 carbon atoms in the molecule.

19. A process according to claim 18 wherein the reaction is performed by adding (iii) to a mixture of (i) and (ii).

20. A process according to claim 1 wherein the reaction is initiated at a temperature below room temperature.

21. A process according to claim 1 wherein (i) is a 1,3-dihalobenzene, a 1,4-dihalobenzene, a 1-hydrocarbyl-3,5-dihalobenzene, a 1,3,5-trihalobenzene, a dihalobiphenyl in which one halogen atom is on each ring, a trihalobiphenyl in which two halogen atoms are on one ring and one halogen atom is on the other ring, a tetrahalobiphenyl in which three halogen atoms are on one ring and one halogen atom is on the other ring, a tetrahalobiphenyl in which two halogen atoms are on one ring and two halogen atoms are on the other ring, a pentahalobiphenyl in which three halogen atoms are on one ring and two halogen atoms are on the other ring, or a hexahalobiphenyl in which three halogen atoms are on one ring and three halogen atoms are on the other ring, a dihalonaphthalene in which one halogen atom is on each ring, a dihalonaphthalene in which both halogen atoms are on the same ring, a trihalonaphthalene in which two halogen atoms are on one ring and one halogen atom is on the other ring, a tetrahalonaphthalene in which two halogen atoms are on one ring and two halogen atoms are on the other ring, or a mixture of any two or more of the foregoing, all with the proviso that all ring halogen atoms of (i) are chlorine atoms or bromine atoms.

22. A process according to claim 21 wherein (i) is free of substitution by functional groups other than said chlorine or bromine atoms.

23. A process according to claim 21 wherein (ii) is a chlorotrialkylsilane or a bromotrialkylsilane in which the alkyl groups each contain in the range of 1 to about 4 carbon atoms.

24. A process according to claim 23 wherein (i) is free of substitution by functional groups other than said chlorine or bromine atoms, and wherein (iii) is a lithium alkyl having in the range of 1 to about 4 carbon atoms in the molecule.

25. A process according to claim 1 wherein (i) is 1,4-dibromobenzene, (ii) is chlorotrialkylsilane or a bromotrialkylsilane in which the alkyl groups each contain in the range of 1 to about 4 carbon atoms, and (iii) is a lithium alkyl having in the range of 1 to about 4 carbon atoms in the molecule.

26. A process according to claim 25 wherein (i) is 1,4-dibromobenzene, (ii) is chlorotriethylsilane, and wherein the reaction is initiated at a temperature below room temperature.

27. A process which comprises forming a mixture from components comprising (i) an arene having a halogen atom of atomic number greater than 9 substituted on at least two non-adjacent carbon atoms with (ii) a halotrihydrocarbylsilane in which the halogen atom has an atomic number greater than 9, and (iii) a hydrocarbyl lithium compound, with the proviso that (ii) and (iii) are not mixed together in the absence of (i), and wherein said components are proportioned such that reaction takes place and a haloarene having at least one trihydrocarbylsilyl ring substituent is formed.

28. A process according to claim 27 wherein (i) is a 1,3-dihalobenzene, a 1,4-dihalobenzene, a 1-hydrocarbyl-3,5-dihalobenzene, a 1,3,5-trihalobenzene, a dihalobiphenyl in which one halogen atom is on each ring, a trihalobiphenyl in which two halogen atoms are on one ring and one halogen atom is on the other ring, a tetrahalobiphenyl in which three halogen atoms are on one ring and one halogen atom is on the other ring, a tetrahalobiphenyl in which two halogen atoms are on one ring and two halogen atoms are on the other ring, a pentahalobiphenyl in which three halogen atoms are on one ring and two halogen atoms are on the other ring, or a hexahalobiphenyl in which three halogen atoms are on one ring and three halogen atoms are on the other ring, a dihalonaphthalene in which one halogen atom is on each ring, a dihalonaphthalene in which both halogen atoms are on the same ring, a trihalonaphthalene in which two halogen atoms are on one ring and one halogen atom is on the other ring, a tetrahalonaphthalene in which two halogen atoms are on one ring and two halogen atoms are on the other ring, or a mixture of any two or more of the foregoing, all with the proviso that all ring halogen atoms of (i) are chlorine atoms or bromine atoms.

29. A process according to claim 28 wherein (i) is free of substitution by functional groups other than said chlorine or bromine atoms.

30. A process according to claim 28 wherein (ii) is a chlorotrialkylsilane or a bromotrialkylsilane in which the alkyl groups each contain in the range of 1 to about 4 carbon atoms.

31. A process according to claim 30 wherein (i) is free of substitution by functional groups other than said chlorine or bromine atoms, and wherein (iii) is a lithium alkyl having in the range of 1 to about 4 carbon atoms in the molecule.

32. A process according to claim 27 wherein the mixture is formed at a temperature below room temperature.

33. A process according to claim 27 wherein (i) is 1,4-dibromobenzene, (ii) is a chlorotrialkylsilane or a bromotrialkylsilane in which the alkyl groups each contain in the range of 1 to about 4 carbon atoms, and (iii) is a lithium alkyl having in the range of 1 to about 4 carbon atoms in the molecule.

34. A process according to claim 33 wherein (i) is 1,4-dibromobenzene, (ii) is chlorotriethylsilane, and wherein the mixture is formed at a temperature below room temperature.

35. A process according to any of claims 27–34 wherein the haloarene having at least one trihydrocarbylsilyl ring substituent formed in the reaction is then reacted with a hydrocarbyl lithium compound to form a lithiated haloarene having at least one trihydrocarbylsilyl ring substituent.

36. A process which comprises
A) forming a mixture from components comprising (i) 1,4-dibromobenzene, (ii) a chlorotrialkylsilane or a bromotrialkylsilane in which the alkyl groups each contain in the range of 1 to about 4 carbon atoms, and (iii) a hydrocarbyl lithium compound, with the proviso that (ii) and (iii) are not mixed together in the absence of (i), and wherein said components are proportioned such that reaction takes place and a 4-halo-1-(trialkylsilyl)benzene is formed;
B) forming a mixture of 4-halo-1-(trialkylsilyl)benzene from A) and a hydrocarbyl lithium compound such that the halogen atom of the 4-halo-1-(trialkylsilyl)benzene is replaced by a lithium atom thereby forming a 4-lithio-1-(trialkylsilyl)benzene;
C) forming a mixture of 4-lithio-1-(trialkylsilyl)benzene from B) and a dihydrocarbylcarbamyl halide such that bis(4-trialkylsilylphenyl)dihydrocarbylamidomethoxy lithium is formed; and
D) forming a mixture of bis(4-trialkylsilylphenyl) dihydrocarbylamidomethoxy lithium from C) and a monomeric substituted or unsubstituted cyclopentadiene or substituted or unsubstituted indene such that a 6,6-di(4-(trialkylsilylphenyl)pentafulvene compound is formed.

37. A process according to claim 36 wherein steps A) through D) are conducted successively in the same reaction vessel without isolation of the reaction products from A), B) or C).

38. A process according to claim 36 wherein (i) is 1,4-dibromobenzene, wherein (ii) is chlorotriethylsilane, wherein (iii) is a lithium alkyl having in the range of 1 to about 4 carbon atoms in the molecule, wherein the hydrocarbyl lithium compound used in B) is a lithium alkyl having in the range of 1 to about 4 carbon atoms in the molecule, wherein the dihydrocarbylcarbamyl halide used in C) is a dialkylcarbamyl chloride in which each alkyl group has in the range of 1 to about 4 carbon atoms, wherein the monomeric substituted or unsubstituted cyclopentadiene or substituted or unsubstituted indene used in D) is a monomeric substituted or unsubstituted cyclopentadiene hydrocarbon, and wherein the reactions in A), B) and C) are initiated at temperatures below room temperature.

39. A process according to claim 38 wherein steps A) through D) are conducted successively in the same reaction vessel without isolation of the reaction products from A), B) or C), and wherein at least the reactions of A), B), and C) are conducted in an ether solvent other than tetrahydrofuran.

40. A process according to claim 39 wherein the reaction of D) is conducted in the presence of both tetrahydrofuran and an ether solvent other than tetrahydrofuran.

41. A process according to claim 39 wherein the reaction of D) is conducted in an ether solvent other than tetrahydrofuran.

* * * * *